US008864695B2

(12) United States Patent
Thornton

(10) Patent No.: US 8,864,695 B2
(45) Date of Patent: Oct. 21, 2014

(54) ADJUSTABLE BRACE APPARATUS

(76) Inventor: Todd M. Thornton, Mission Viejo, CA (US)

(*) Notice: Subject to any disclaimer, the term of this patent is extended or adjusted under 35 U.S.C. 154(b) by 722 days.

(21) Appl. No.: 13/079,135

(22) Filed: Apr. 4, 2011

(65) Prior Publication Data

US 2012/0253251 A1 Oct. 4, 2012

(51) Int. Cl.
*A61F 5/00* (2006.01)
*A61F 5/02* (2006.01)

(52) U.S. Cl.
CPC ..................................... *A61F 5/028* (2013.01)
USPC ................ 602/19; 602/5; 128/96.1; 128/99.1

(58) Field of Classification Search
CPC ....... A61F 5/028; A61F 5/0585; A41F 11/16; A41F 9/002
USPC ........... 602/5, 19; 2/310–312; 128/96.1, 98.1, 128/100.1, 101.1, 97.1, 99.1, 876
See application file for complete search history.

(56) References Cited

U.S. PATENT DOCUMENTS

| | | | |
|---|---|---|---|
| 5,503,620 A | 4/1996 | Danzger | |
| RE35,940 E | 10/1998 | Heinz et al. | |
| 5,853,378 A | 12/1998 | Modglin | |
| 5,911,697 A | 6/1999 | Biedermann et al. | |
| 5,967,998 A | 10/1999 | Modglin | |
| 6,213,968 B1 | 4/2001 | Heinz et al. | |
| 6,322,529 B1 | 11/2001 | Chung | |
| 6,478,759 B1 | 11/2002 | Modglin et al. | |
| 6,610,022 B1 | 8/2003 | Ashbaugh et al. | |
| 6,666,838 B2 | 12/2003 | Modglin et al. | |
| 6,676,617 B1 | 1/2004 | Miller | |
| 6,676,620 B2 | 1/2004 | Schwenn et al. | |
| 6,840,916 B2 | 1/2005 | Kozersky | |
| 6,926,685 B1 | 8/2005 | Modglin | |
| 6,932,780 B2 | 8/2005 | Kozersky | |
| 6,951,547 B1 | 10/2005 | Park et al. | |
| 6,964,644 B1 | 11/2005 | Garth | |
| 7,001,348 B2 | 2/2006 | Garth et al. | |
| 7,025,737 B2 | 4/2006 | Modglin | |
| 7,083,585 B2 | 8/2006 | Latham | |
| 7,101,348 B2 | 9/2006 | Garth et al. | |
| 7,118,543 B2 | 10/2006 | Telles et al. | |
| 7,186,229 B2 | 3/2007 | Schwenn et al. | |
| 7,201,727 B2* | 4/2007 | Schwenn et al. | 602/12 |
| 7,306,571 B2* | 12/2007 | Schwenn et al. | 602/12 |
| 7,316,660 B1 | 1/2008 | Modglin | |
| 7,329,231 B2 | 2/2008 | Frank | |
| 7,556,608 B2 | 7/2009 | Parizot | |
| 7,727,172 B2 | 6/2010 | Wang | |
| 8,142,377 B2* | 3/2012 | Garth et al. | 602/5 |
| 8,303,528 B2* | 11/2012 | Ingimundarson et al. | 602/19 |

(Continued)

*Primary Examiner* — Kim M Lewis
(74) *Attorney, Agent, or Firm* — One3 IP Management, P.C.; Justin G. Sanders; Jeromye V. Sartin

(57) ABSTRACT

An adjustable brace apparatus provides, in an exemplary embodiment, a pair of elongate wings configured for wrapping about and substantially conforming to a portion of a body of a user, an adjustment sleeve configured for slidably receiving each of the wings, and a pair of first and second tightening segments removably engagable with each of the wings and slidably engaged and suspended within the adjustment sleeve, thereby enabling the wings to substantially float and selectively overlap atop one another within the adjustment sleeve. In use, the user is able to selectively position, wrap, and engage the wings around the user's body portion, and selectively draw the wings closer against the user's body portion.

20 Claims, 9 Drawing Sheets

(56) References Cited

U.S. PATENT DOCUMENTS

| | | | |
|---|---|---|---|
| 8,328,742 B2 * | 12/2012 | Bledsoe | 602/19 |
| 2005/0251074 A1 * | 11/2005 | Latham | 602/19 |
| 2005/0267390 A1 * | 12/2005 | Garth et al. | 602/19 |
| 2006/0206992 A1 | 9/2006 | Godshaw et al. | |
| 2008/0004557 A1 | 1/2008 | Wolanske | |
| 2009/0082707 A1 | 3/2009 | Rumsey | |
| 2009/0163841 A1 | 6/2009 | Garth | |
| 2009/0192425 A1 * | 7/2009 | Garth et al. | 602/19 |
| 2009/0204042 A1 * | 8/2009 | Park | 602/19 |
| 2009/0204043 A1 | 8/2009 | Smith, Jr. | |
| 2010/0100019 A1 | 4/2010 | Chen et al. | |
| 2010/0121240 A1 | 5/2010 | Smith | |
| 2010/0168630 A1 * | 7/2010 | Cropper et al. | 602/19 |
| 2010/0217167 A1 | 8/2010 | Ingimundarson et al. | |
| 2010/0268141 A1 * | 10/2010 | Bannister | 602/19 |
| 2011/0213284 A1 * | 9/2011 | Garth et al. | 602/19 |
| 2012/0245502 A1 * | 9/2012 | Garth et al. | 602/19 |
| 2013/0090585 A1 * | 4/2013 | Bue et al. | 602/19 |
| 2013/0158457 A1 * | 6/2013 | Garth et al. | 602/19 |

* cited by examiner

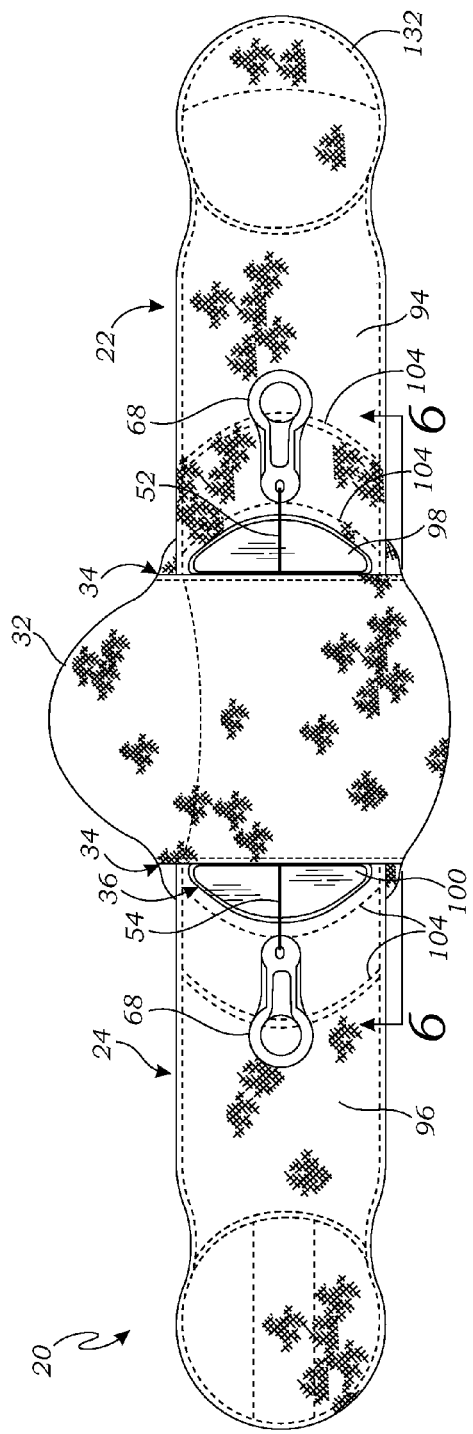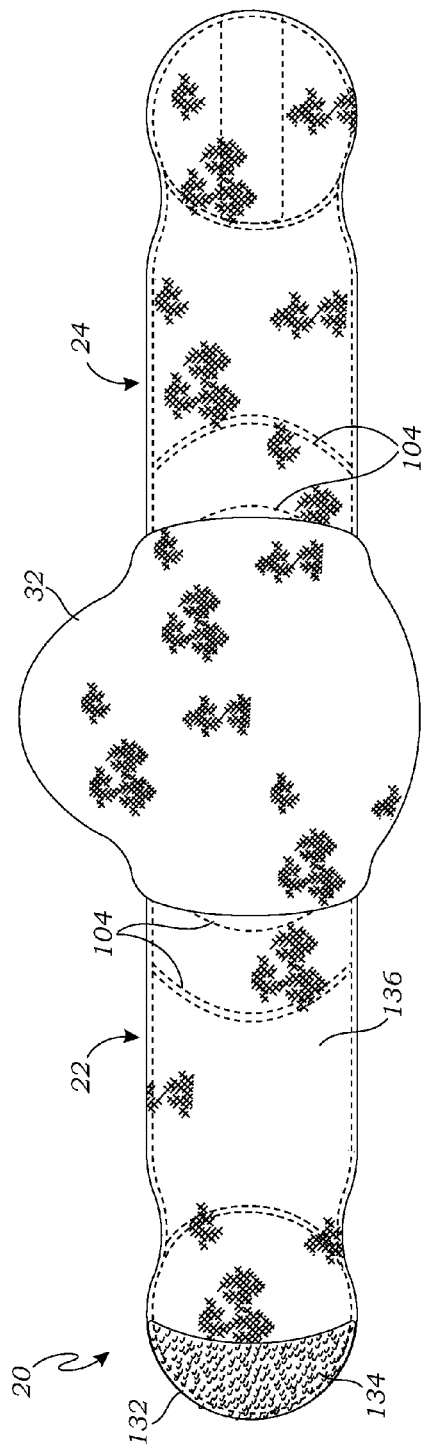
Fig. 1
Fig. 2

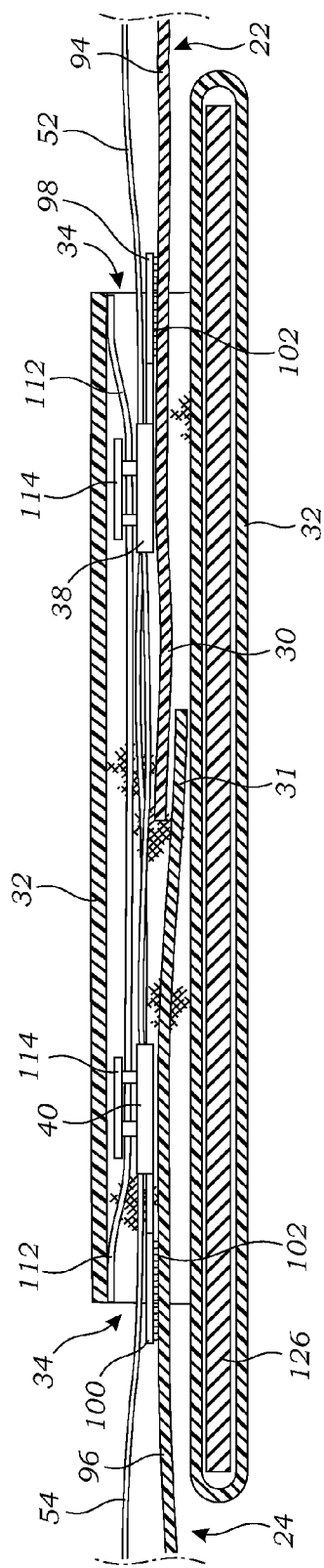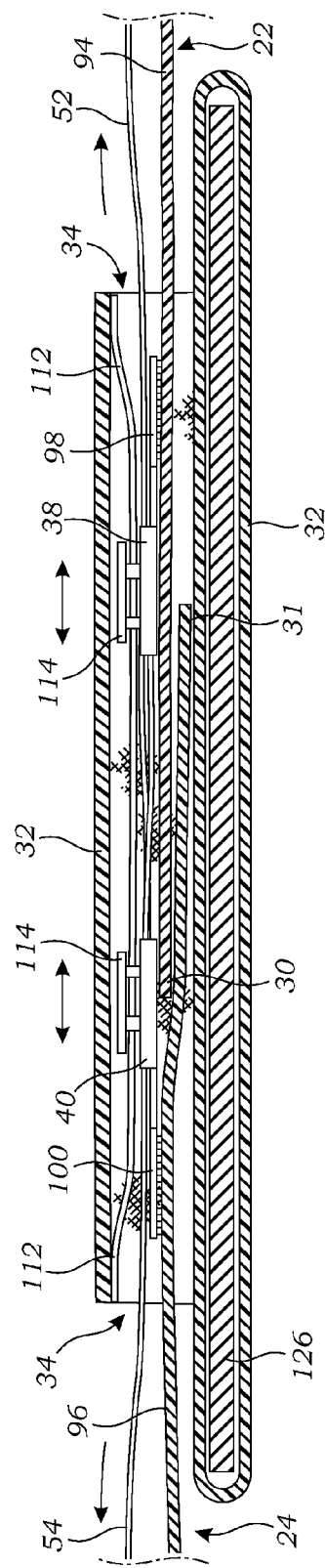
Fig. 6
Fig. 7

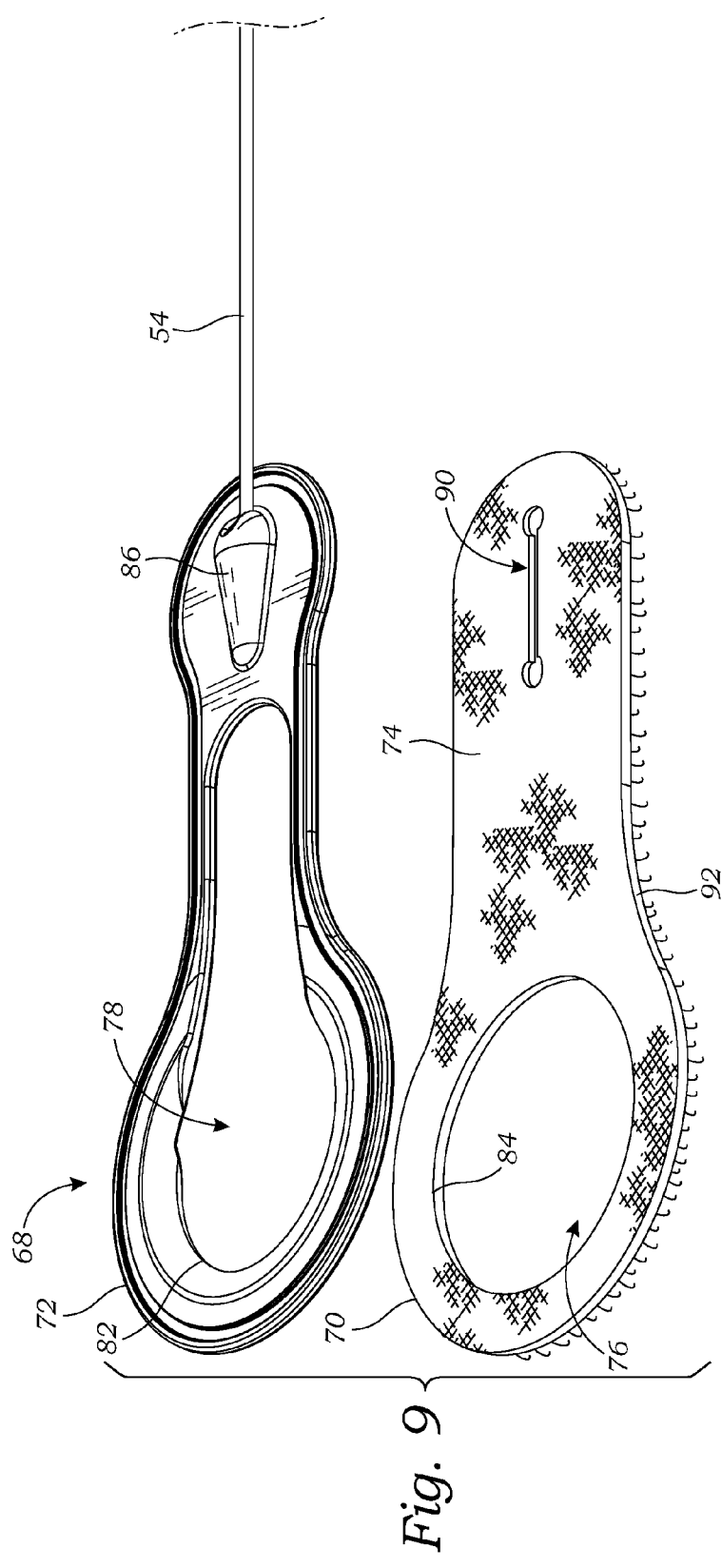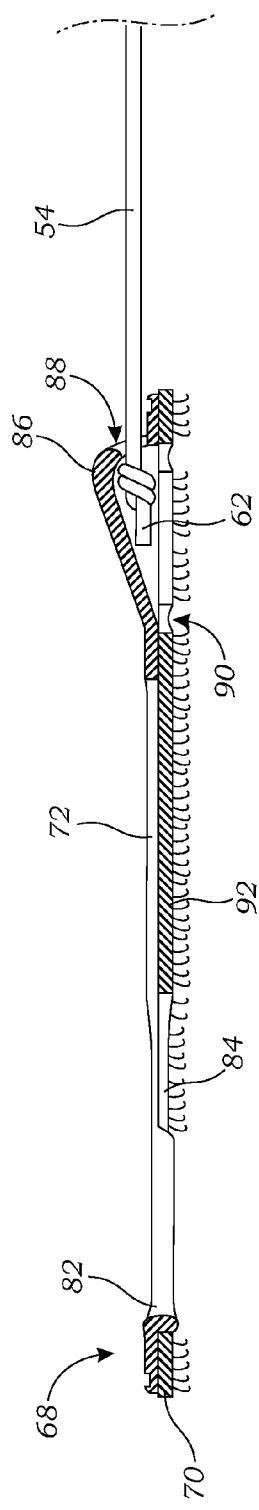

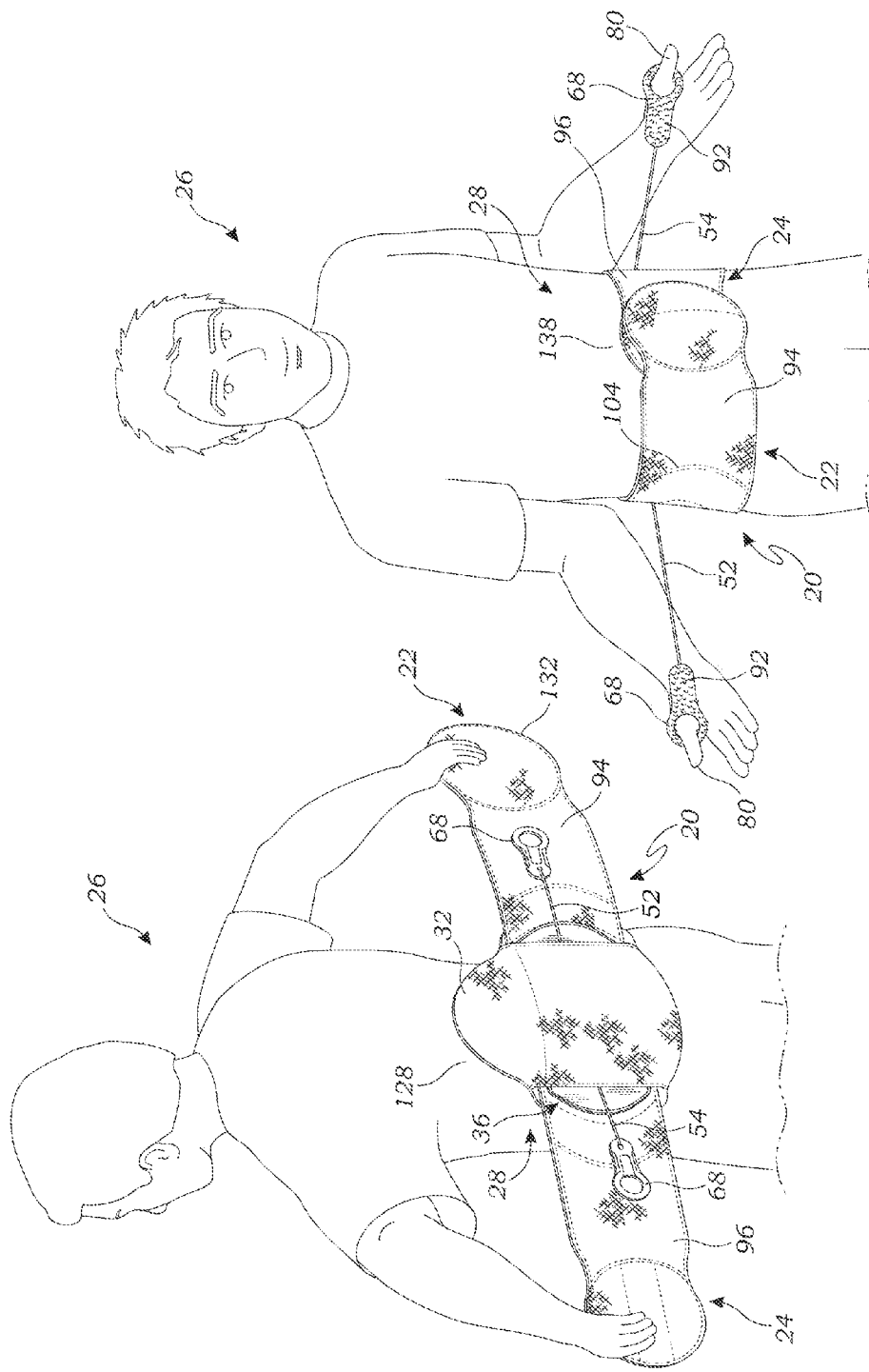

ADJUSTABLE BRACE APPARATUS

RELATED APPLICATIONS

Not applicable.

INCORPORATION BY REFERENCE

Applicants hereby incorporate herein by reference any and all U.S. patents and U.S. patent applications cited or referred to in this application.

BACKGROUND OF THE INVENTION

1. Field of the Invention

Aspects of this invention relate generally to support braces, and more particularly to an adjustable brace configured for being selectively resizable to accommodate a wide range of users and body portions.

2. Description of Related Art

A common method of alleviating pain in people suffering from back injuries, promoting healing in post-operative back surgery patients, and reducing the likelihood of experiencing such injuries in the first place, is to stabilize the spine by means of an orthosis, such as a brace. Such braces include a multitude of materials and designs which can be snugly fitted around the patient's trunk or torso. Similar braces may be used in connection with other body parts, on both humans and non-human patients.

The following art defines the present state of this field:

U.S. Pat. No. 5,503,620 to Danzger is generally directed to a back support belt comprising a primary support belt including fasteners for fastening the same generally at the frontal area of the waist of the wearer, and a secondary tensioning belt comprising fasteners for fastening the same around the primary support belt generally at the frontal area of the waist of the wearer is provided, and includes back support belt color tensioning indicators on the secondary tensioning belt which are visible only from the rear and side areas of the waist of the wearer, and thus not by the wearer, and which are operable to indicate both when the back support belt is properly tensioned around the waist of the wearer, and when the back support belt is not properly tensioned around the waist of the wearer. The back support belt color tensioning indicators are operable to indicate proper and improper tensioning of the support belt independently of the relationship between the size of the support belt and the waist size of the wearer to thus be virtually foolproof in operation. For use in instances wherein the wearer of the back support belt is forced to work in the absence of anyone qualified to observe the color tensioning indicators on the secondary tensioning belt, the back support belt will further include an additional color tensioning indicator taking the form of non-obscurable alignment marks formed on one of the primary support belt fasteners and co-operable with one of the secondary tensioning belt fasteners to indicate proper back support belt tensioning. The additional color tensioning indicator is not, however, operable independently of the relationship between the size of the support belt and the waist size of the wearer, and are thus not foolproof in operation.

U.S. Pat. No. RE35,940 to Heinz et al. is generally directed to a back brace apparatus which has electromechanical means for tightening a brace around the trunk of a patient to a desired tension. The electromechanical means is controllable by the patient to effect predetermined tension settings. A cable and pulley arrangement tightened by a motor provides a mechanical advantage so that the brace may be tightened by a small motor. A microprocessor controls the motor to obtain the desired repeatable tension settings.

U.S. Pat. Nos. 5,853,378 and 5,967,998 to Modglin are generally directed to a lumbo-sacral orthopedic brace apparatus formed of flexible materials to fit over a patient's torso and having a front flexible section shaped to fit over the front of a patient's torso and covered with a hook and loop fastener loop material. A plurality of flexible straps are attached to the brace front section on either side thereof by being attached to a hook and loop fastener hook strap which is attached to the brace front section loop material. A rear flexible section is shaped to fit over the rear of a patient's torso and has a plurality of loops attached to each side thereof by being attached to a hook and loop hook strap which is attached to the brace rear section loop material. The hook straps are able to be attached to the front or to the back at any angle at any point across the entire front or back, respectively, rapidly altering the orthosis to accommodate a broad range of figure types. The straps on the front flexible section are looped through the loops on the rear section and are connected in groups to common flexible straps. Pulling one common strap pulls a plurality of straps through the loops. Each common strap has hook material attached thereto so that the common strap can be attached to the front section loop material in different positions and angles to adjust the stress of the rear flexible member on the rear of a patient's torso.

U.S. Pat. No. 5,911,697 to Biedermann et al. is generally directed to a spinal column orthosis system which reduces the requirements for stock-keeping various sizes of spinal column orthosis and which enables a better adaptation to the body. The inventive spinal column orthosis comprises a rear member of predetermined height and width, a front member and two side members each connecting the rear member with the front member.

U.S. Pat. No. 6,213,968 to Heinz et al. is generally directed to an orthotic device which includes an orthosis body adapted to be wrapped around the torso of a wearer of the device, the orthosis body having at least two segments in juxtaposed relationship. Means are provided at free end portions of the at least two segments to releasably secure the free end portions to one another. At least two cables are provided, each cable operatively connected to the at least two segments. At least two sets of pulleys are mounted on the at least two segments with each cable operatively connected to the at least two segments running through a pulley on each of the at least two segments in alteration, shortening of each cable pulling the at least two segments together and tightening the orthotic device with the aid of a mechanical advantage dependent upon the number of pulleys mounted on each of the at least two segments.

U.S. Pat. No. 6,322,529 to Chung is generally directed to a detachment type waist protecting belt wherein hook and loop fastener strips are attached to distal ends and height-wise middle portions of left and right bands, a pair of connecting plates made of a soft plastic material are secured to proximal ends of the left and right bands, connection rings are rotatably fastened to the connecting plates by pins to be spaced one from another in a longitudinal direction by a predetermined distance, both ends of a pair of pulling cords respectively pass zigzag from upper and lower ends of the connecting plates through the connection rings so as to be freed at height-wise middle portions of the connecting plates, and a pair of tightening bands are connected to the freed both ends of the pulling cords. The detachment type waist protecting belt includes a waist support which fits a contour of the waist of the human body. Guide projections are formed at both sides of an outer surface of the waist support. The height-wise middle portions of the left and right bands are defined with guide slots which extend in a transverse direction to guide the guide projections, whereby the detachment type waist protecting belt can be equipped with the waist support as occasion arises.

U.S. Pat. No. 6,478,759 to Modglin et al. is generally directed to a thoraco-lumbo-sacral brace formed of flexible materials designed to fit patients of varying shapes and sizes. The brace comprises an anterior support and a posterior support, both made of a hook and loop material, and connected by two sets of connection straps. The connection straps comprise a series of flexible straps attached to a common strap, and a rigid strap. Each flexible strap passes through a loop attached to the posterior support. The common strap is made of a hook and loop material. The common strap may be fastened to the anterior support at any angle in order to tighten the brace and adjust it to fit a variety of body types. The rigid strap similarly passes through a loop and is attached to the anterior support atop the common strap, thereby minimizing unwanted lateral motion. The anterior support further may accept a plurality of splints sized to fit within a plurality of cavities located on the front side of the anterior support. These splints provide additional support for the patient. Lateral panels may be attached between the anterior support and posterior support to widen the brace. A thoracic lumbar support may be attached to the posterior support, providing increased support for a patient's upper back. A sternal extension may be attached to the anterior support, thus providing additional bracing for a patient's chest.

U.S. Pat. No. 6,676,617 to Miller is generally directed to an adjustable, removable, interlocking iliac crest belt for a body brace. The belt can be secured to the inside of a posterior portion of the body brace, and is secured about the patient's waist and upper hip region, engaging the iliac crests of the patient and providing additional pressure and stabilization force. Adjustable hook and loop fastening elements can be used to fasten the iliac crest belt. The belt is intended for use in body braces of the type for immobilizing or stabilizing a patient's spine in a post-surgical therapeutic application, or for treating abnormal spinal curvature, which brace may include body-conforming front and back shell elements molded from plastic, and adjustable strap elements affixed thereto for attaching the shells together around the torso of the patient with a selected compressive force.

U.S. Pat. No. 6,676,620 to Schwenn et al. is generally directed to an orthosis comprising a first body member that can conform to a portion of a patient's body and a second body member that can conform to another portion of a patient's body. A closure unit having a first connector member with a first plurality of support posts can be operatively connected to the first body member, while a second connector member with a second plurality of support posts can be operatively connected to the second body member. An elongated flexible pull member can operatively extend between the respective first and second support posts so that when tightened by a patient, a pull member slides across the support posts to provide a mechanical force advantage to draw the first body member and the second body member against the patient's torso. A closure unit can be of a modular configuration for subjective mounting on various components of an orthosis to provide a highly adaptable closure unit.

U.S. Pat. No. 6,610,022 to Ashbaugh et al. is generally directed to a fastener system for an orthopedic device having separable, spaced apart first posterior and second anterior sections. The system uses sets of straps, complimentary clips, cooperating fixed anchor ring assemblies and pull ring assemblies to quickly ensure accurate and proper alignment of the device to the user's body.

U.S. Pat. No. 6,666,838 to Modglin et al. is generally directed to a low-profile lumbo-sacral orthosis consisting of flexible anterior and posterior members, both shaped to fit around the waist of a patient's torso, and a closure system on each side of the orthosis for joining the flexible anterior and posterior members. The anterior member is formed of a web of flexible material. A middle panel of loop material is attached to external surface of the anterior web in the middle to form a pocket, and two anterior side panels of loop material are attached to external surface of the anterior web at each side to form pockets. Reinforcing splints are inserted into each pocket. The flexible posterior member is formed of a web of flexible material with two posterior side panels of loop material attached to the external surface to form two pockets. Reinforcing splints are inserted into each of the pockets. A moldable posterior splint is attached to the external surface of the posterior web in the middle. Each closure system consists of a plurality of straps and buckles connected to attachment strip. The straps are connected to the anterior attachment strip, extend through the plurality of buckles on the posterior attachment strip, and terminating in a common strap.

U.S. Pat. No. 6,840,916 to Kozersky is generally directed to a custom-fit spinal orthosis which includes a pair of semi-rigid side panels configured to fit in close-fitting relationship to a wearer's torso. Each side panel includes an anterior edge disposed in overlapping releasably fixed relationship to the other side panel to enclose a major portion of the front of a wearer's torso. The posterior edges of each side panel are disposed near the spinal column of the wearer and are releasably fixed to a discrete posterior panel overlying a length of the wearer's spine. The posterior panel and the side panel are provided with cooperating vertically spaced horizontally extending slots aligned with vertically spaced openings to accept releasably fixed fasteners to connect the side panels and posterior panel together in an adjustable relationship. The posterior panel is heat-deformable for shaping into a rigid curve conforming to the wearer's lumbar curve to provide a high degree of anatomically desirable support for the wearer's spine in cooperating relationship with the side panels mounted in close-fitting relationship to the wearer's torso.

U.S. Pat. No. 6,926,685 to Modglin is generally directed to a strap system for use with a brace of the type having a first shell generally conforming to a first body part of a user and a second shell generally conforming to a second body part of the user. The strap system includes a first strap and a first buckle located on the first strap, a second strap and a second buckle located on the second strap, a plurality of slides securable to the second shell for receiving the straps, a first latch member securable to a first portion of the first shell, and a second latch member securable to a second portion of the first shell.

U.S. Pat. No. 6,932,780 to Kozersky is generally directed to a spinal orthosis having discrete left and right side belt-like segments configured to wrap around a wearer's torso and be adjustably connected in the front and rear portions of the side segments. Each belt-like segment includes an anterior and posterior edges disposed in overlapping relationship to one another. Fastening means are provided for releasably connecting the anterior overlapping portions to initially mount the orthosis around the wearer's waist. The posterior portion of the orthosis includes a semi-rigid or rigid lumbar support panel to which the overlapping posterior portions of each side segment are adjustably connected via a plurality of slots and aligned holes in either the panel or the side segments and a fastener extended through a respective aligned hole and slot. The fasteners are permitted to slide within the confines of the respective slots to modify the effective circumferential girth defined by the side segments. A pair of straps are attached to the posterior end portions of each segment and extend in opposing directions for releasably fixing to a frontal portion of a belt-like segment to permit the wearer to increase or decrease the compressive forces applied by the orthosis.

U.S. Pat. No. 6,951,547 to Park et al. is generally directed to a waist support frame for a detachment type waist protecting belt to hold the vertebra region of a vertebra related patient. The frame is comprised of, including but not limited to, two plastic plates. Each of the plates has a window at the center and one guiding nut on the center of the exterior side of the inner-half of the rim. The two plates are connected by two hinges, which are attached to the upper and the lower parts of the plastic plates, to form a saddle like shape that fits the contour of the waist of an individual patient dynamically.

U.S. Pat. No. 6,964,644 to Garth is generally directed to a back brace having left, right and back panels that substantially overlap to form a tubular back brace when worn. Leverage multiples tightening force during tightening. After each successive tightening by the lever, retaining bands retain the back brace in position. Pressure spreading layers have a secondary adjustment mechanism comprising a plurality of notches extending inward from upper and lower edges, and at least one hole aligned with each of the plurality of notches. The back panel has a window overlying the sacrum. The orthopedist can observe the engagement of the back brace in this area through the window. A malleable bar is attached to the back panel adjacent the window so that the orthopedist can adjust the malleable bar for proper fit. After the initial fitting, including adjustment of the back panel over the sacrum, the back brace may be readily donned and doffed by the patient.

U.S. Patent Application Publication No. 2005/0267390 to Garth et al. is generally directed to a double pull body brace comprising a one-piece panel which engages around the torso and overlaps at the front. At the overlap, it is attached to itself by means of a hook-and-loop fastener so that a wide range of adjustment is possible. In the back, spaced cord guides are mounted on said panel. Each cord guide carries a plurality of cord guide lobes. An upper cord is engaged around the upper cord guide lobes, and a lower cord is engaged around the lower cord guide lobes. These cords are separately attached to pull tabs. When donned, the user pulls on the pull tabs to separately adjust upper and lower closure tension of the body brace. When in correct adjustment, the pull tabs are attached in place by hook-and-loop fasteners.

U.S. Pat. No. 7,001,348 to Garth et al. is generally directed to a double pull body brace comprising a one-piece panel which engages around the torso and overlaps at the front. At the overlap, it is attached to itself by means of a hook-and-loop fastener so that a wide range of adjustment is possible. In the back, spaced cord guides are mounted on said panel. Each cord guide carries a plurality of cord guide lobes. An upper cord is engaged around the upper cord guide lobes, and a lower cord is engaged around the lower cord guide lobes. These cords are separately attached to pull tabs. When donned, the user pulls on the pull tabs to separately adjust upper and lower closure tension of the body brace. When in correct adjustment, the pull tabs are attached in place by hook-and-loop fasteners.

U.S. Pat. No. 7,025,737 to Modglin is generally directed to a spinal orthosis which includes a posterior support having a substantially rigid posterior splint, an anterior support having a substantially rigid anterior splint, and a pair of overlapping supports having substantially rigid splints are releasably attachable to the posterior support. The rigid splints of the overlapping supports overlap a portion of the posterior splint and the anterior splint when the orthosis is installed on a user.

U.S. Pat. No. 7,083,585 to Latham is generally directed to a string arrangement for a detachment type waist-protecting belt to hold the vertebra region of a vertebra related patient. The string arrangement enables a separate fastening of the upper portion and lower portion of the belt to form a saddle like shape that fits the contour of the waist of an individual patient dynamically with or without the extra support of a frame. The waist-protecting belt can also be connected to a back supporting frame, which is comprised of two plastic plates, via two guiding nuts, fixed on the center of the exterior side of the inner-half of the rim of each solid plastic plate, guided through the two narrow and long holes found on the wider portions of the belt, and held in place by two wide head bolts which screw on to the nuts. Then the upper portion and lower portion of the frame is adjusted separately by the movement of the upper and lower portion of the belt.

U.S. Pat. No. 7,101,348 to Garth et al. is generally directed to a lower torso support having first and second front panels that are attachable to each other and independently moveable with respect to the side portions of the support. The front panels can be any suitable dimensions. However, slipper shapes are deemed to be the most useful, with front panels preferably at least 15 cm long and at least 6 cm tall at their tallest point. In preferred embodiments the front panels are readily attachable to and detachable from the side portions in a wide variety of superior to inferior and medial to lateral positions. At present the preferred mechanism for making those connections is a hook and loop mechanism, which has the advantage of also allowing the front panels to be angled with respect to the side portions in any suitable orientation.

U.S. Patent Application Publication No. 2006/0206992 to Godshaw et al. is generally directed to a multipart tool belt which includes a central segment and adjustable length lateral side segments which may be joined together to provide a customized belt for use as part of a tool belt assembly.

U.S. Pat. No. 7,118,543 to Telles et al. is generally directed to a closure system for orthosis that permits a first body member conforming to a portion of a patient's torso to be connected through the closure system, with a second body member conforming to another portion of a patient's torso. The closure system includes a first connector member with a first series of plastic molded channels and a second connector member with a second series of plastic molded channels with an elongated flexible pull member operatively weaving around the respective first and second series of plastic molded channels to provide a mechanical force advantage when tightened by the patient to draw the first body member and the second body member against the patient's torso to exert compression forces. The elongated flexible pull member can comprise a cord such as a polyester cord with an exterior braided configuration.

U.S. Pat. Nos. 7,186,229, 7,201,727, and 7,306,571 to Schwenn et al. are generally directed to an orthosis comprising a first body member that can conform to a portion of a patient's body and a second body member that can conform to another portion of a patient's body. A closure unit having a first connector member with a first plurality of support posts can be operatively connected to the first body member, while a second connector member with a second plurality of support posts can be operatively connected to the second body member. An elongated flexible pull member can operatively extend between the respective first and second support posts so that when tightened by a patient, a pull member slides across the support posts to provide a mechanical force advantage to draw the first body member and the second body member against the patient's torso. A closure unit can be of a modular configuration for subjective mounting on various components of an orthosis to provide a highly adaptable closure unit.

U.S. Patent Application Publication No. 2008/0004557 to Wolanske is generally directed to an equalizing back brace adapted to be worn by a person. The back brace includes a band adapted to encircle the wearer's torso. The band has a rear portion adapted to be positioned proximate the spine of a wearer, has side portions extending away from the rear portion at opposite directions, and has marginal end portions that are adapted to overlap one another proximate the front of such wearer. These marginal end portions are adapted to be selectively secured to another to complete and close a band which encircles the wearer's torso. Two tightening mechanisms are mounted on the side portions of the band. Each tightening mechanism has an intermediately-pivoted member, has an upper trace secured to the band and engaging an upper marginal end portion of the member, and has a lower trace secured to the band and engaging a lower marginal end portion of the member. A pull strip is mounted on the band, and engages an intermediate portion of the member. The pull strip is adapted to be secured to the associated side portion at any of a plurality of positions relative thereto. Either or both side of the pull strips may be grasp, and pulled away from the rear portion, and secured to the band to selectively tighten the band about the wearer's torso.

U.S. Pat. No. 7,316,660 to Modglin is generally directed to a spinal orthosis for treating a spine, which includes an anterior support and a posterior support, each support made of a laminate having a flexible foam material and a substantially rigid plastic sheet material sandwiched between a pair of soft flexible sheet materials and bonded together to yield a unitary and substantially rigid laminate material.

U.S. Pat. No. 7,329,231 to Frank is generally directed to a brace for supporting both the abdomen and lower back of the user. The brace includes a preformed abdominal support member and a preformed lumbar support member having an ideal lumbar shape with a circular dome that is vertically bisected by an oblong, elliptical protrusion, the support members each joined by two belts. The belts are positioned through slots on each member and are used to select the biasing force needed for each user. The device further includes rounded corners with indented edges and surface vents on each support member for the user's comfort during sporting events or strenuous activity.

U.S. Patent Application Publication No. 2009/0082707 to Rumsey is generally directed to a modular type body brace worn about a portion of the body, and one or more removably attached body panels associated with the body brace for supporting the portion of the body. The body panels are preferably contoured to the physiology of the portion of the body and have a relatively thicker core and progressively thinner peripheral region to provide dynamic flex response when supporting the portion of the body.

U.S. Patent Application Publication No. 2009/0163841 to Garth is generally directed to a lumbar support which includes a flexible lumbar piece mechanically coupled to a back panel, and a rotatable adjusting member, preferably a dial accessible by the wear, that adjusts the extent the lumbar piece bows away from the back panel. A series of detents can be used to provide discrete "stops". Lumbar pieces can comprise any suitable material, including for example metal or plastic, and are preferably removable from the back panel.

U.S. Pat. No. 7,556,608 to Parizot is generally directed to a device for supporting lumbar vertebras and/or sacrospinal muscles, generally called a lumbar belt. The device comprises a back lumbar supporting part and two lateral parts which are connected to the said back part and provided with additional closing means arranged on the free front ends thereof. The external surface of the back part comprises fixing means which interact with additional fixing means connected to the free back ends of the lateral parts in such a way that it is possible to close the belt without overlapping the said lateral parts on the abdominal region of a patient.

U.S. Patent Application Publication No. 2009/0192425 to Garth et al. is generally directed to a body brace for a wearer having a combination of adjustment mechanisms and fasteners to help fit the body brace to a wearer. A wearer first fastens the body brace about his abdomen and lumbar regions to generally fit the body brace around the wearer's waist. The wearer then adjusts one set of adjustment mechanisms that adjust an upper and lower circumference of the brace to allow the brace to fit both straight and pear-shaped bodies. Lastly, the wearer adjusts a second set of adjustment mechanisms that tighten a rear panel of the body brace against a lumbar region of the wearer. Preferably, the adjustment mechanism that is used to tighten the rear panel is an advantaged adjustment mechanism to allow for fine-tuning and a snug fit.

U.S. Patent Application Publication No. 2009/0204043 to Smith, Jr. is generally directed to a lumbar support device and a selective stabilization support device for use in treating mechanical lower back pain. The lumbar support device includes a semi-rigid member for positioning around the user's abdomen. The semi-rigid member helps to prevent excessive trunk bending by the patient. At least one and preferably two tensioning straps are also provided connectable at first and second end regions to a surface of the semi-rigid member. The strap or straps are provided to encircle the user's torso to maintain the lumbar support device in position. An adjustable attachment means, for example in the form of a clip, is attached to the straps. The adjustable attachment means is movable laterally along the strap. A pad base is provided on the adjustable attachment means, the pad base being movable with the adjustable attachment means such that its position at the lumbar region of the patient can be varied.

U.S. Patent Application Publication No. 2010/0100019 to Chen et al. is generally directed to a device for supporting the abdominal region of the user. A fabric band is sized to be worn surrounding the abdominal region which supports strategically placed hook and loop regions. A pair of segments of stretch material, also having hook and loop regions at least one of their ends are capable of being selectively and removably appended to the fabric band to apply compression or restriction to the user's abdomen. The device is particularly useful in helping one to restore abdominal muscle and control particularly after pregnancy.

U.S. Patent Application Publication No. 2010/0121240 to Smith is generally directed to a lumbar support device and a selective stabilization support device for use in treating mechanical back pain. The lumbar support device includes a torso belt for positioning around the user's mid-section. At least two and typically three straps are also provided connectable at first and second end regions to a surface of the torso belt. Straps are provided to encircle the user's torso to maintain the lumbar support device in position and to engage and maintain in position a pressure appliance arm having a pressure pad thereon. The pressure pad is may thus be configured and precisely positioned to relieve symptoms of back pain.

U.S. Pat. No. 7,727,172 to Wang is generally directed to a back brace which includes a first brace member having a first connector, and a second brace member having a second connector and a coupler at two opposite sides thereof. The coupler is detachably connectable to the first connector. A first adjustment holder is affixed to one end of the first brace member and holds therein a first rod member. A second adjustment holder is affixed to one end of the second brace member and holds therein a second rod member. Two pull cords are inserted through the first adjustment holder and the second adjustment holder and run alternately back and forth over the first rod member and the second rod member to adjustably and abuttably hold the first and second brace members side by side. Two fastening members are fastened to distal ends of the pull cords and detachably connectable to the first and second connectors.

U.S. Patent Application Publication No. 2010/0217167 to Ingimundarson et al. is generally directed to an orthopedic device in the form of a lumbar support which includes first and second elongate belt members, an anatomically shaped plate, and a closure system connecting the belt members to the plate. The closure system is arranged to move the belt members relative to the plate, and connects to the belt members via a flexible belt attachment which removably secures to the belt members. The closure system includes tensioning elements corresponding to the belt members, and a pulley system connecting to the tensioning elements. The closure system is slidably mounted to the plate and arranged to the belt members relative to the plate between opposed linear directions. The plate has various contours which provide pressure distribution over a lumbar region of a back. Anatomically shaped and resiliently formed handles secure to the tensioning elements and the belt members.

The prior art described above teaches various adjustable brace-like devices, including adjustable back braces having at least one flexible brace segment, or wing, to be wrapped around the user along with a tightening means removably engagable therewith for further tightening the wing or wings against the user. However, the prior art fails to teach such an adjustable brace having an adjustment sleeve configured for allowing the tightening means to be slidably engaged and float therewithin, thereby enabling the wings to selectively overlap within the adjustment sleeve as needed in order to create a comfortable, selectively re-adjustable, "one size fits all" brace. Aspects of the present invention fulfill these needs and provide further related advantages as described in the following summary.

SUMMARY OF THE INVENTION

Aspects of the present invention teach certain benefits in construction and use which give rise to the exemplary advantages described below.

Aspects of the present invention are directed to solving these problems by providing an adjustable brace apparatus comprising, in an exemplary embodiment, a pair of elongate first and second wings configured for wrapping about and substantially conforming to a portion of a body of a user, such as a torso. An adjustment sleeve is configured for slidably receiving a first end of each of the first and second wings through opposing ends of the adjustment sleeve. The adjustment sleeve is further configured for allowing the first ends of the wings to selectively overlap atop one another therewithin, thereby creating a relatively low-profile brace with substantially no uncomfortable bunching of material within the adjustment sleeve. An opposing free second end of each of the first and second wings provides a means for removable engagement with one another. A tightening means is slidably engaged and suspended within the adjustment sleeve. The tightening means comprises a first tightening segment removably engagable with an outer surface of the first wing, and a second tightening segment removably engagable with an outer surface of the second wing, with an at least one cord operatively connected to the first and second tightening segments. A plurality of substantially perpendicular tightening posts are mounted within each of the first and second tightening segments, with the at least one cord running around a tightening post on each tightening segment in alternation for providing a mechanical force advantage when pulled by the user, dependent upon the number of tightening posts mounted within each tightening segment, to draw the first and second wings closer against the user's body portion. In use, with the first ends of each of the first and second wings slidably inserted into the opposing ends of the adjustment sleeve and overlapped as necessary so as to substantially approximate the circumference of the user's body portion, and with the tightening means removably engaged with the first and second wings, the user is able to selectively position and wrap the first and second wings around the user's body portion, engage the free second ends, and selectively pull the at least one cord of the tightening means to create further compression. Thus, aspects of the present invention provide a solution to the above discussed shortcomings of the prior art.

A primary objective inherent in the above described apparatus and method of use is to provide advantages not taught by the prior art.

Another objective is to provide such an apparatus that is capable of adjusting and re-adjusting to accommodate a wide range of body portion shapes and sizes.

A further objective is to provide such an apparatus that allows a user to selectively adjust and tighten the apparatus with relative ease.

A still further objective is to provide such an apparatus that creates a comfortable, ergonomic, substantially low-profile support brace for the user's body portion that can be worn either over or underneath the user's clothing.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings:

FIG. 1 is a top plan view of an exemplary embodiment of the invention;

FIG. 2 is a bottom plan view thereof;

FIGS. 6 and 7 are partial cross-sectional views taken along line 6-6 in FIG. 1;

FIG. 9 is an exploded view of a pull ring of the exemplary embodiment;

FIG. 10 is a cross-sectional view taken along line 10-10 in FIG. 5;

FIG. 14 is a rear perspective view of the user wrapping the first and second wings of the exemplary embodiment around their torso; and FIG. 15 is a front view of the user pulling a first cord and a second cord of the exemplary embodiment for selectively contracting the tightening means.

DETAILED DESCRIPTION OF THE INVENTION

Figure 3:
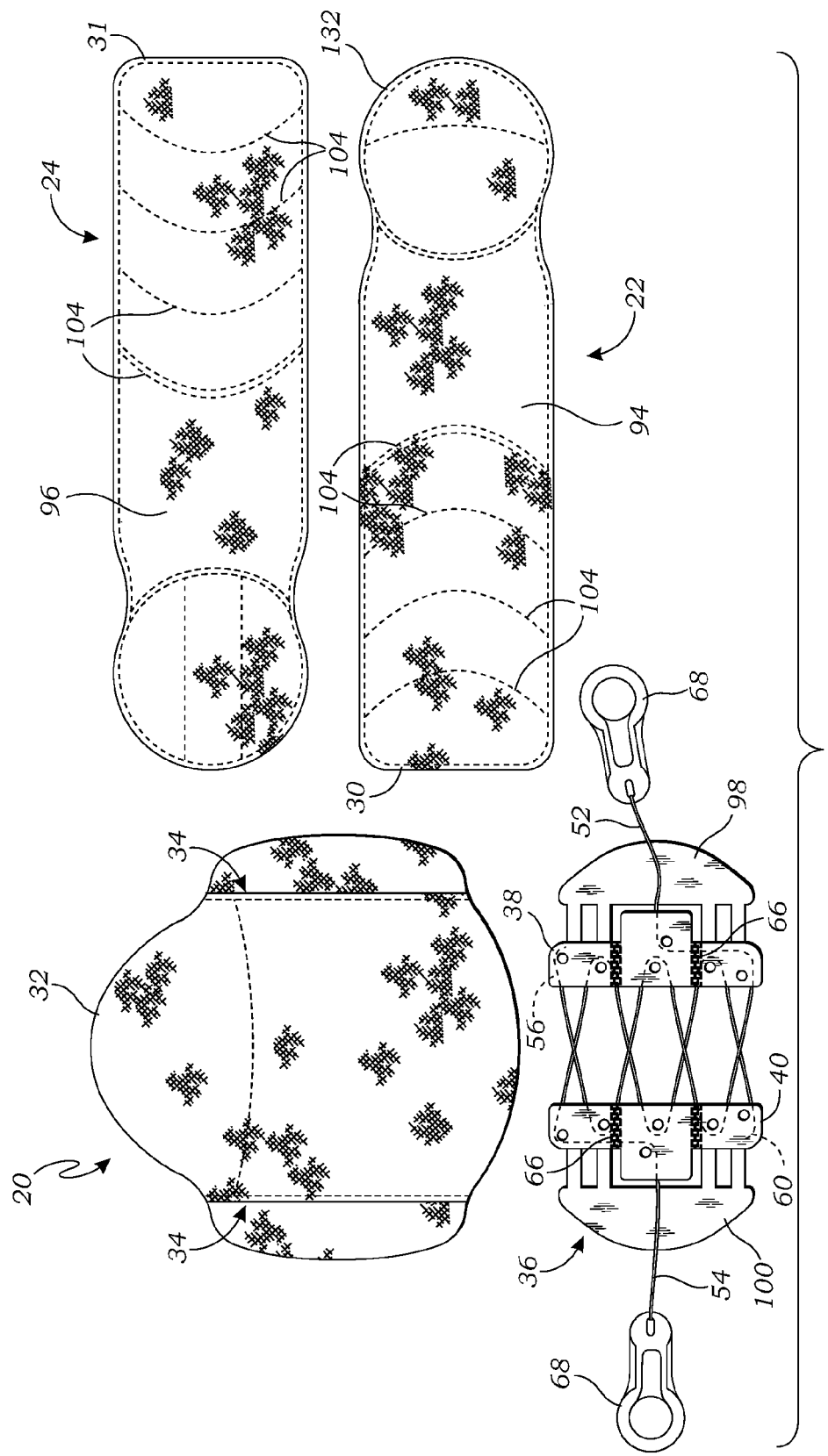
FIG. 3 is a top plan view thereof, with each of the first and second wings, adjustment sleeve, and tightening means disengaged and separated from one another.

The above described drawing figures illustrate aspects of the invention in at least one of its exemplary embodiments, which are further defined in detail in the following description.

Turning now to FIG. 1, there is shown a top plan view of an exemplary embodiment of an adjustable brace apparatus 20. The apparatus 20 comprises, in one embodiment, a pair of elongate first and second wings 22 and 24 configured for wrapping about and substantially conforming to a portion of a body of a user 26. In the exemplary embodiment, the portion about which the first and second wings 22 and 24 wrap is a torso 28 of the user 26 (FIGS. 14 and 15). It should be noted that, for illustrative and clarity purposes, the present invention is herein shown and described in the context of engagement about the torso 28 of the user 26. However, the scope and applicability of the present invention should not be read as being so limited. In fact, the present invention may be sized and configured, in further embodiments, to be used in connection with virtually any body part, belonging to a human or non-human user, that is capable of being wrapped and supported, such as an arm or a leg.

The first and second wings 22 and 24 are preferably constructed of a soft, relatively flexible material, such as a padded fabric. However, other materials, now known or later developed, may be substituted in further embodiments that allow the wings 22 and 24 to substantially carry out each of the functions herein described. Additionally, while the first and second wings 22 and 24 are two separate pieces in the exemplary embodiment, in alternate embodiments, the wings 22 and 24 may actually be a unitary, elongate piece. In yet further embodiments, a first end 30 and 31 of each of the wings 22 and 24 are connected by an at least one relatively thin, flexible joining member, such as a relatively thinner piece of fabric, configured for substantially allowing the wings 22 and 24 to selectively overlap during use of the apparatus 20.

Figure 4:
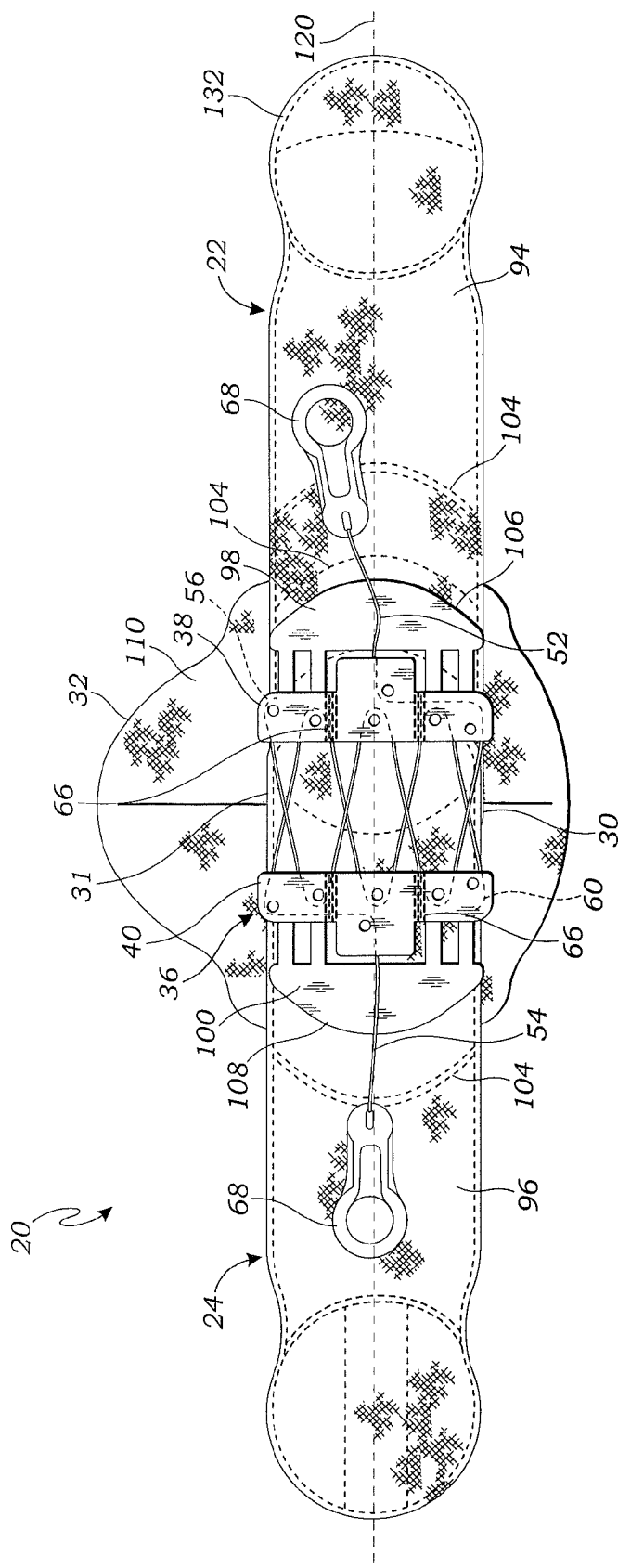
FIG. 4 is a top plan view thereof, with a portion of the adjustment sleeve cut away for clarity.

With continued reference to FIG. 1, as well as FIG. 3, an adjustment sleeve 32, also preferably made of a padded fabric, is configured for slidably receiving the first end 30 and 31 of each of the first and second wings 22 and 24 through opposing open ends 34 of the adjustment sleeve 32. As shown in the cutaway view of FIG. 4, and as described in greater detail below, the adjustment sleeve 32 is also configured for allowing the first ends 30 and 31 of the first and second wings 22 and 24 to selectively overlap atop one another therewithin; thereby creating a relatively low-profile brace with substantially no uncomfortable bunching of material within the adjustment sleeve 32 during use.

Figure 8:
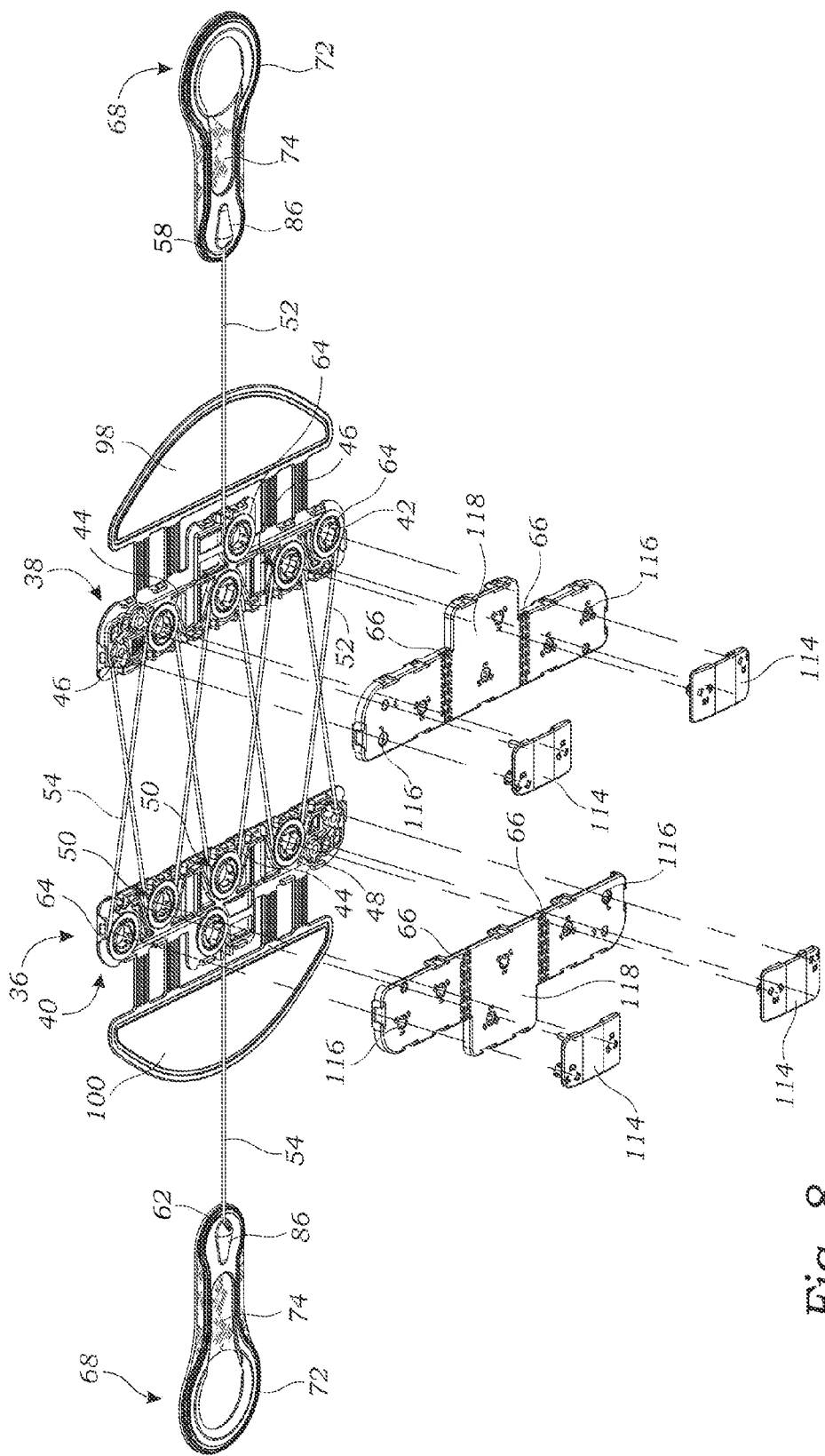
FIG. 8 is an exploded view of the tightening means of the exemplary embodiment.

As best shown in FIGS. 3 and 8, the apparatus 20 also provides a tightening means 36 slidably engaged and suspended within the adjustment sleeve 32. In the exemplary embodiment, the tightening means 36 is a cable-block tightening array comprising a first tightening segment 38 and an opposing second tightening segment 40. The first tightening segment 38 provides a plurality of spaced apart, substantially perpendicular first tightening posts 42 mounted therewithin, along with corresponding substantially U-shaped walls 44 spaced from the first tightening posts 42, forming substantially U-shaped first cord channels 46 therebetween. Similarly, the second tightening segment 40 provides a plurality of second tightening posts 48 and second cord channels 50. A first cord 52 is operatively connected to the first tightening segment 38 and a second cord 54 is operatively connected to the second tightening segment 40, with each of the first and second cords 52 and 54 running through alternating first and second cord channels 46 and 50 and around alternating first and second tightening posts 42 and 48, much like a corset, for providing a mechanical force advantage when pulled by the user 26, dependent upon the number of tightening posts 42 and 48 mounted within each tightening segment 38 and 40, to draw the first and second wings 22 and 24 closer against the user's body portion during use. In a bit more detail, in the exemplary embodiment, a fixed end 56 of the first cord 52 is secured within the first tightening segment 38. The first cord 52 then runs around alternating first and second tightening posts 42 and 48 in alternation, as best shown in FIG. 8, with a free end 58 of the first cord 52 exiting out of the first tightening segment 38 (i.e., the same tightening segment 38 in which the fixed end 56 of the first cord 52 is secured). The second cord 54 has a similar interconnection with the second tightening segment 40, with a fixed end 60 of the second cord 54 being secured within the second tightening segment 40 and a free end 62 of the second cord 54 exiting out of the second tightening segment 40. These operative connections between the first and second cords 52 and 54 and the first and second tightening segments 38 and 40 function to substantially increase both the efficiency and the proportional amount of contraction of the tightening means 36 as the user 26 selectively pulls the first and second cords 52 and 54 during use. It should be noted that, in further embodiments, the exact arrangement of the cords 52 and 54 and tightening posts 42 and 48 may take on other configurations, now known or later developed, that enable the tightening means 36 to carry out substantially the same functionality herein described.

In the exemplary embodiment, with continued reference to FIG. 8, the efficiency of the contraction functionality of the tightening means 36 is further improved by providing a bearing 64 rotatably engaged with each of the first and second tightening posts 42 and 48. Each of the bearings 64 is configured for substantially reducing the amount of friction between the corresponding cord 52 or 54 and tightening post 42 or 48 as the cord 52 or 54 moves through the tightening means 36. This reduction in friction, in turn, reduces the amount of resistance that the user 26 must overcome in order to selectively pull and contract the tightening means 36 during use.

As shown best in FIG. 8, each of the first and second tightening segments 38 and 40 also preferably provides an at least one longitudinal flexing means 66 configured for allowing the tightening means 36 to selectively flex inwardly, toward the user's body portion, and substantially conform to the contours of the user's body portion during use of the apparatus 20. In the exemplary embodiment, the flexing means 66 are integral with the first and second tightening segments 38 and 40, comprising relatively thinner, partially perforated sections that allow the selective flexing of the tightening segments 38 and 40 to occur. Additionally, the portions of the tightening segments 38 and 40 positioned directly underneath each of the flexing means 66, including portions of the substantially U-shaped walls 44, are also relatively thinner than the remainder of the tightening segments 38 and 40 in the exemplary embodiment. This configuration not only allows the tightening means 36 to selectively flex as needed, but also assists in substantially maintaining the overall structural integrity of the relatively rigid tightening means 36, to better ensure that the contraction functionality of the tightening means 36 is not compromised. In further embodiments, the flexing means 66 may comprise any other structure or material, now known or later developed, that substantially enables the tightening means 36 to carry out this same functionality.

With continued reference to FIG. 8, the free end 58 and 62 of each of the first and second cords 52 and 54 is preferably integral with a pull ring 68 sized and configured for allowing the user 26 to easily grasp and pull each of the first and second cords 52 and 54 in order to selectively contract the tightening means 36. In the exemplary embodiment, as best shown in FIGS. 9 and 10, each pull ring 68 comprises a thin, relatively resilient first portion 70 and a thin, relatively rigid second portion 72 integrally secured to a top surface 74 of the first portion 70. The first portion 70 defines a first ring aperture 76 and the second portion 72 defines a similar second ring aperture 78, each sized and configured for allowing the user 26 to insert an at least one finger or thumb 80 therethrough to assist in selectively pulling the corresponding cord 52 or 54. Additionally, the second ring aperture 78 provides a rounded annular second inner edge 82 which extends a distance through the first ring aperture 76, substantially obscuring a first inner edge 84 of the first ring aperture 76 in order to provide a more comfortable, ergonomic means for the user 26 to selectively pull the corresponding cord 52 or 54. As shown best in the cross-sectional view of FIG. 10, the first and second portions 70 and 72 together provide a cord capsule 86 therebetween, configured for capturing the free end 58 or 62 of the corresponding cord 52 or 54 therewithin. The cord capsule 86 provides a first cord aperture 88 configured for allowing the corresponding cord 52 or 54 to extend into the cord capsule 86. Additionally, the first portion 70 provides a second cord aperture 90 positioned and configured for providing access to the free end 58 or 62 of the cord 52 or 54 within the cord capsule 86. During manufacture, the free end 58 or 62 of the cord 52 or 54 is inserted through both the first and second cord apertures 88 and 90 and is then knotted so that the free end 58 or 62 is unable to be pulled back through the first cord aperture 88. The cord 52 or 54 is then pulled back through the second cord aperture 90 into the cord capsule 86, where it is substantially preserved from any potential damage or disengagement through use of the apparatus 20.

In the exemplary embodiment, the second portion 72 is made of a relatively rigid, molded thermoplastic material. The first portion 70 is preferably made of hook-and-loop material. More specifically, the top surface 74 of the first portion 70 provides loop material, while an opposing bottom surface 92 of the first portion 70 provides hook material. An outer surface 94 and 96 of each of the first and second wings 22 and 24 also provides loop material, thereby enabling each of the pull rings 68 to be removably engagable with the wings 22 and 24 when the pull rings 68 are not being used. Preferably, the loop material covers the entire outer surface 94 and 96 of each of the first and second wings 22 and 24, whether secured to the wings 22 and 24 or integral with the fabric material of which the wings 22 and 24 are constructed, to allow selective engagement of the pull rings 68 anywhere on the outer surface 94 and 96 of either wing 22 and 24. Additionally, as best shown in FIG. 9, the second portion 72 is preferably configured for allowing at least partial access to the loop material on top surface 74 of the first portion 70. This configuration enables each of the pull rings 68 to selectively overlap and be at least partially removably engaged with one another, in addition to being removably engaged with the outer surface 94 and 96 of the wings 22 and 24, in the event such overlapping engagement is required based on the circumference size of the user's body portion and the distance by which each of the wings 22 and 24 extends into the adjustment sleeve 32. It should be noted that, in alternate embodiments, the first and second portions 70 and 72 may be constructed of any other materials, or combination of materials, now known or later developed, that enable the pull rings 68 to substantially carry out the functionality herein described. Additionally, other types of removable engagement means, now known or later developed, between the pull rings 68 and the wings 22 and 24 may also be substituted in further embodiments.

Referring again to FIG. 4, the first tightening segment 38 provides, in the exemplary embodiment, an integral, relatively flat first connector portion 98. The second tightening segment 40 provides a similar second connector portion 100. Each of the first and second connector portions 98 and 100 are configured for removable engagement with the outer surface 94 and 96 of the first and second wings 22 and 24, respectively. In the exemplary embodiment, this removable engagement is achieved using hook material positioned on a bottom surface 102 of each connector portion 98 and 100 for engaging the loop material positioned on the outer surface 94 and 96 of each wing 22 and 24; much like the pull rings 68. As shown best in FIG. 13, this configuration enables the tightening means 36 to be selectively positionable anywhere on, and engagable with, the outer surface 94 and 96 of each of the wings 22 and 24. The importance of this is discussed further below. In alternate embodiments, other types of removable engagement means now known or later developed, may be substituted.

It should be noted that, in the exemplary embodiment, each component of the tightening means 36, other than the cords 52 and 54, is preferably made of a molded thermoplastic. Furthermore, the exemplary embodiment of the present invention is preferably free from any type of metal components, which is highly beneficial in medical imaging applications in which the present invention may be used. In further embodiments, however, these components may be constructed from other materials, now known or later developed, including metal.

As shown best in FIG. 3, the outer surface 94 and 96 of each of the first and second wings 22 and 24 preferably provides a plurality of size indicia 104 positioned and configured for assisting the user 26 in consistently positioning each of the first and second tightening segments 38 and 40 on the first and second wings 22 and 24, respectively, in order to achieve a consistent circumference size for the apparatus 20 (i.e., small, medium, large, extra-large, etc.). In the exemplary embodiment, the size indicia 104 are stitched into each of the wings 22 and 24. However, in alternate embodiments, the size indicia 104 may be formed using any permanent or non-permanent technique now known or later developed, such as printing directly onto the outer surface 94 and 96 of each wing 22 and 24. In the exemplary embodiment, the shape of each size indicia 104 approximates the shape of the connector portions 98 and 100. This enables the user 26 to selectively align a leading edge 106 and 108 of each connector portion 98 and 100 with the appropriate size indicia 104, depending on the circumference size of the user's body portion, before engaging the connector portions 98 and 100 with the wings 22 and 24. Certainly, though, given the fact that the connector portions 98 and 100 are capable of being positioned and removably engaged substantially anywhere on the outer surface 94 and 96 of each wing 22 and 24 in the exemplary embodiment, the tightening array 36 may be selectively positioned anywhere thereon, thereby allowing for any number of circumference sizes, so that the user 26 may create a custom fit.

Figure 5:
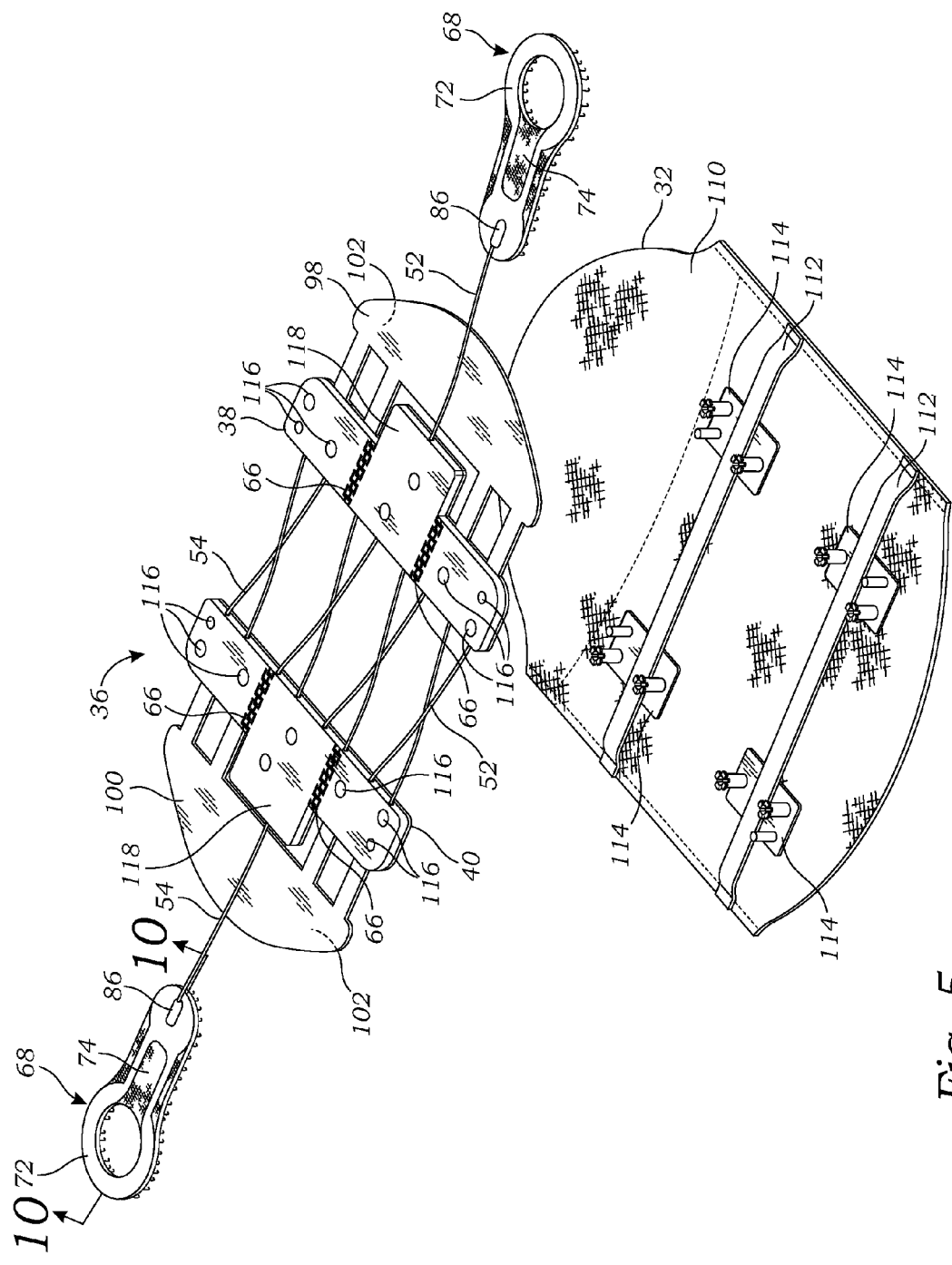
FIG. 5 is a perspective view of the adjustment sleeve and tightening means of the exemplary embodiment, illustrating the exemplary engagement therebetween.

As mentioned above, the tightening means 36 is slidably engaged and suspended within the adjustment sleeve 32. In the exemplary embodiment, as shown best in FIG. 5, an inner surface 110 of the adjustment sleeve 32 provides a pair of elongate, relatively flexible, substantially laterally oriented segment tracks 112. Each of the segment tracks 112 is configured for slidably receiving and retaining an at least one track engagement means provided by the first tightening segment 38 and an at least one further track engagement means provided by the second tightening segment 40. In the exemplary embodiment, each of the track engagement means is a track clip 114 configured for removable engagement with a plurality of clip apertures 116 positioned on a top surface 118 of the corresponding tightening segment 38 or 40. In further embodiments (not shown), the track engagement means comprises a slot integral with the top surface 118 of each of the tightening segments 38 and 40 and configured for slidable engagement with the segment tracks 112. In still further embodiments, this slidable engagement may be achieved using any other structure or configuration, now known or later developed, that is capable of substantially enabling the tightening means 36 to be slidably engaged and suspended within the adjustment sleeve 32.

As shown best in the partial cross-sectional views of FIGS. 6 and 7, the slidable engagement with the segment tracks 112 and inner surface 110 of the adjustment sleeve 32 enables the tightening means 36 to substantially float within the adjustment sleeve 32. As such, the tightening means 36 is able to move and selectively contract and expand during use with relatively little friction or resistance. Furthermore, with the outer surface 94 and 96 of the first and second wings 22 and 24 removably engaged with the bottom surface 102 of the first and second connector portions 98 and 100, respectively, the wings 22 and 24 are able to substantially float within the adjustment sleeve 32 as well. This configuration allows the wings 22 and 24 to lay end-to-end or selectively overlap atop one another within the adjustment sleeve 32, thereby creating a relatively low-profile brace with substantially no uncomfortable bunching of the wings 22 and 24 within the adjustment sleeve 32 during use, regardless of the distance by which each of the wings 22 and 24 extends into the adjustment sleeve 32. Additionally, as shown in FIG. 7, even as the tightening means 36 is selectively contracted, thereby bringing the wings 22 and 24 into further overlapping contact, the wings 22 and 24 are still able to remain substantially flat within the adjustment sleeve 32. Thus, regardless of the circumference size of the user's body portion, the apparatus 20, once adjusted to accommodate the body portion, is able to maintain a relatively flat profile by virtue of the suspended, slidable engagement of the tightening means 36 and wings 22 and 24. This allows the apparatus 20 to be comfortably worn either above or underneath the user's clothing.

It should be noted that, in addition to the above mentioned benefits, the slidable engagement between the segment tracks 112 of the adjustment sleeve 32 and the tightening means 36 also assists in substantially maintaining the tightening means 36 in the proper position within the adjustment sleeve 32, thereby better ensuring that the tightening means 36 and the wings 22 and 24 do not unintentionally move out of position during use. The segment tracks 112 also assist in assuring that the direction of contraction and expansion of the tightening means 36 is generally along a center axis 120 (FIG. 4) of the wings 22 and 24, ensuring optimal functionality of the tightening means 36 during use.

Figure 11:
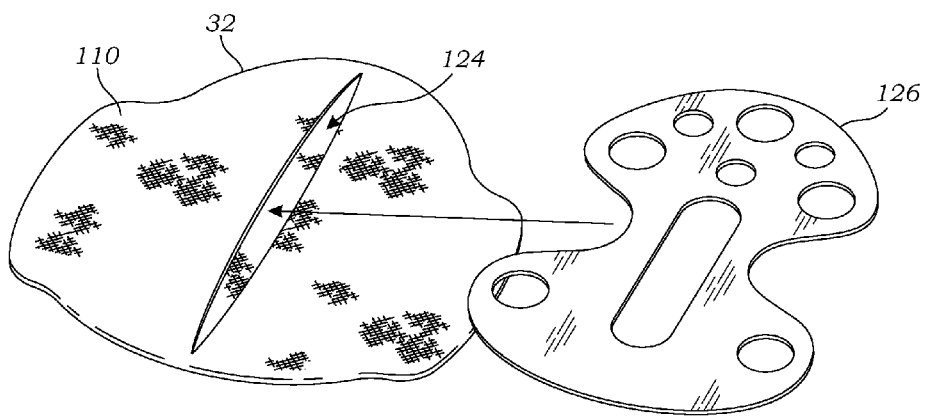
FIG. 11 is a perspective view of a relatively rigid support insert removed from a pocket of the adjustment sleeve of the exemplary embodiment, with a portion of the adjustment sleeve cut away for clarity.

Turning to FIG. 11, the inner surface 110 of the adjustment sleeve 32 also preferably provides a pocket 124 sized and configured for removably receiving a relatively rigid support insert 126. The support insert 126 is sized and configured for providing further structural and ergonomic support to the user's body portion during use of the apparatus 20. In the exemplary embodiment, the support insert 126 is configured for providing support to a lower back 128 of the user 26.

Figure 12:
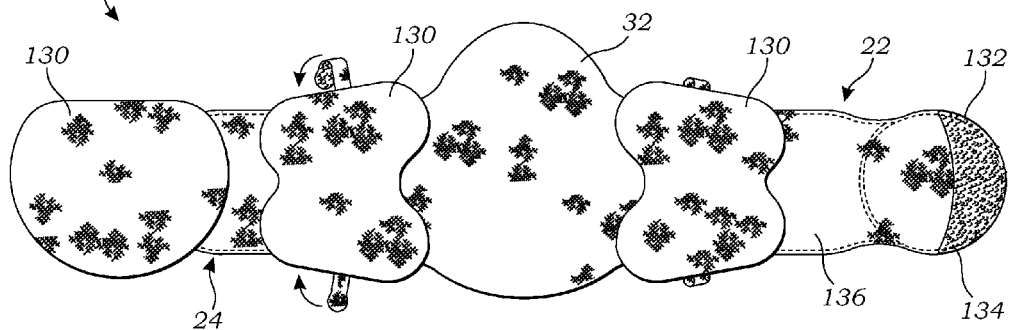
FIG. 12 is a bottom plan view of the exemplary embodiment of the invention, illustrating various relatively rigid wing panels that may be selectively positionable on and removably engagable with the first and second wings.

As shown in FIG. 12, the apparatus 20 may provide even further structural and ergonomic support, in further embodiments, using one or more relatively rigid wing panels 130 selectively positionable on and removably engagable with the first and second wings 22 and 24. Similar to the other components of the present invention, each of the wing panels 130 is preferably engagable with the wings 22 or 24 using hook-and-loop fasteners. However, other fasteners, now known or later developed, may be substituted. In still further embodiments (not shown), the apparatus 20 may provide further peripheral components configured for removable engagement with the wings 22 and 24 or adjustment sleeve 32 and capable of providing further structural and/or therapeutic functionality. Such peripheral components may include, but are not limited to, heating means, cooling means, therapeutic stimulation means, or vibrating means.

Referring back to FIGS. 1 and 2, an opposing free second end 132 of the first wing 22 provides a means for removable engagement with the outer surface 96 of the second wing 24, thereby enabling the apparatus 20 to be removably engaged about the desired body portion of the user 26, such as the user's torso 28. In the exemplary embodiment, the means for removable engagement comprises hook-and-loop material. More specifically, a portion 134 of an inner surface 136 of the first wing 22, proximal the second end 132, provides hook material. As mentioned above, the entire outer surface 96 of the second wing 24 provides loop material. Thus, the hook material of the first wing 22 is able to engage the loop material of the second wing 24, regardless of the circumference size of the user's body portion or the distance by which the first ends 30 and 31 of the wings 22 and 24 are positioned within the adjustment sleeve 32. It should be noted that, in further embodiments, other means for removable engagement, now known or later developed, may be substituted.

Figure 13:
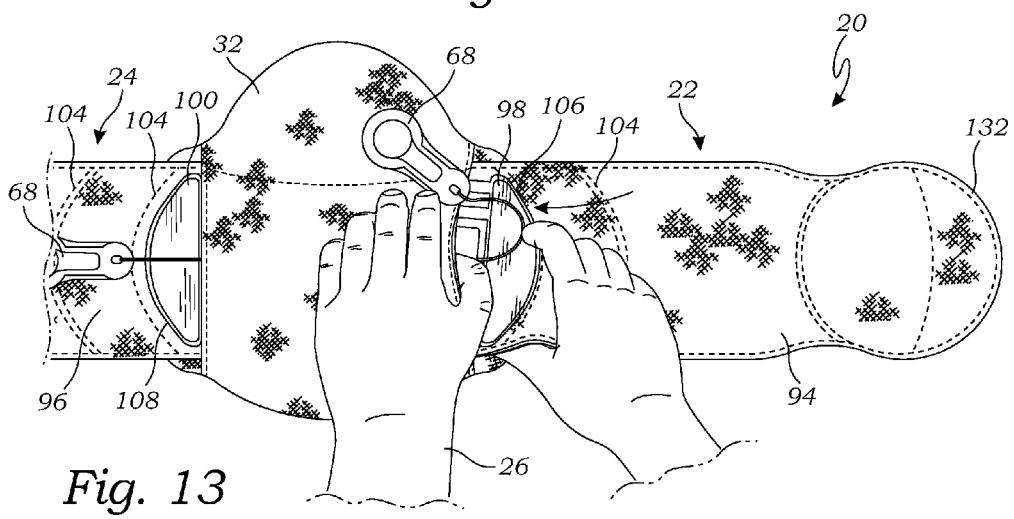
FIG. 13 is a top perspective view of a user selectively inserting and engaging one of the first and second wings within the adjustment sleeve.

FIGS. 13-15 show the exemplary embodiment of the apparatus 20 in use, with the desired body portion to be supported being the torso 28 of the user 26. Referring first to FIG. 13, the first ends 30 and 31 of the wings 22 and 24 are slidably inserted into the opposing open ends 34 of the adjustment sleeve 32 and overlapped as necessary, in order to create the appropriate circumference size to approximate the circumference of the user's torso 28. Using the appropriate size indicia 104, the first and second connector portions 98 and 100 of the tightening means 36 are then positioned and removably engaged with the outer surface 94 and 96 of each of the wings 22 and 24. Next, as shown in FIG. 14, the user 26 selectively positions the adjustment sleeve 32 substantially adjacent the lower back 128, then wraps the wings 22 and 24 around the torso 28 and engages the free second end 132 of the first wing 22 with the outer surface 96 of the second wing 24, substantially adjacent an abdomen 138 of the user 26. Finally, as shown in FIG. 15, the user selectively pulls the first and second cords 52 and 54 to contract the tightening means 36, drawing the wings closer 22 and 24 together and, thus, creating further compression of the apparatus 20 against the torso 28. Once the apparatus 20 is sufficiently tightened against the user's torso 28, the user 26 engages each of the pull rings 68 with the outer surface 94 and 96 of the wings 22 and 24.

Given the ability of the first and second wings 22 and 24 to be selectively inserted a desired distance into the adjustment sleeve 32, along with the ability of the tightening means 36 to be selectively removably engagable substantially anywhere on the outer surface 94 and 96 of the wings 22 and 24, the apparatus 20 is capable of allowing the user 26 to always size the apparatus 20 such that it is engaged about the user's body portion in a substantially optimal position; regardless of the circumference size of the user's body portion. For example, in the exemplary embodiment, the optimal position of the apparatus 20 is with the adjustment sleeve 32 positioned substantially adjacent the lower back 128 and the second end 132 of the first wing 22 engaged with the outer surface 96 of the second wing 24 in a position substantially adjacent the abdomen 138.

Furthermore, this removable engagement between the wings 22 and 24 and the tightening means 36 also enables the user 26 to selectively engage, interchange, and use wings of varying shapes and sizes, depending on the body portion to be wrapped and supported as well as the particular needs of the user 26.

To summarize, regarding the exemplary embodiments of the present invention as shown and described herein, it will be appreciated that an adjustable brace apparatus is disclosed and configured for being selectively resizable to accommodate a wide range of users and body portions. Because the principles of the invention may be practiced in a number of configurations beyond those shown and described, it is to be understood that the invention is not in any way limited by the exemplary embodiments, but is generally directed to an adjustable brace apparatus and is able to take numerous forms to do so without departing from the spirit and scope of the invention. Furthermore, the various features of each of the above-described embodiments may be combined in any logical manner and are intended to be included within the scope of the present invention.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. An adjustable brace apparatus comprising:
a pair of elongate first and second wings configured for wrapping about and substantially conforming to a portion of a body of a user;
an adjustment sleeve configured for slidably receiving a first end of each of the first and second wings through opposing ends of the adjustment sleeve, the first ends capable of selectively overlapping atop one another therewithin;
a tightening means slidably engaged and suspended within the adjustment sleeve, the tightening means comprising:
a first tightening segment removably engagable with an outer surface of the first wing;
a second tightening segment removably engagable with an outer surface of the second wing;
an at least one cord operatively connected to the first and second tightening segments; and
a plurality of substantially perpendicular tightening posts mounted within each of the first and second tightening segments, with the at least one cord running around a tightening post on each tightening segment in alternation for providing a mechanical force advantage when pulled by the user, dependent upon the number of tightening posts mounted within each tightening segment, to draw the first and second wings closer against the user's body portion; and
an opposing free second end of each of the first and second wings providing a means for removable engagement with one another;
whereby, during use of the apparatus, with the first ends of each of the first and second wings slidably inserted into the opposing ends of the adjustment sleeve and overlapped as necessary so as to substantially approximate a circumference of the user's body portion, and with the tightening means removably engaged with the first and second wings, the user is able to selectively position and wrap the first and second wings around the user's body portion, engage the free second ends, and selectively pull the at least one cord of the tightening means to create further compression.

2. The adjustable brace apparatus of claim 1, wherein the means for removable engagement of the opposing free second ends of the first and second wings comprises hook-and-loop material.

3. The adjustable brace apparatus of claim 2, wherein a portion of an inner surface of the first wing, proximal the second end, provides hook material.

4. The adjustable brace apparatus of claim 3, wherein substantially an entirety of the outer surface of each of the first and second wings provides loop material.

5. The adjustable brace apparatus of claim 1, wherein the first and second tightening segments each provides a plurality of substantially U-shaped cord channels formed by U-shaped walls spaced from the substantially perpendicular tightening posts.

6. The adjustable brace apparatus of claim 5, wherein each of the substantially perpendicular tightening posts provides a bearing rotatably engaged therewith and configured for reducing friction between the at least one cord and the tightening post.

7. The adjustable brace apparatus of claim 6, wherein the tightening means comprises a first cord operatively connected to the first tightening segment and a second cord operatively connected to the second tightening segment, each of the first and second cords running through alternating cord channels and around alternating tightening posts on each tightening segment in alternation.

8. The adjustable brace apparatus of claim 7, wherein a free end of each of the first and second cords is integral with a pull ring.

9. The adjustable brace apparatus of claim 8, wherein a bottom surface of each of the pull rings is configured for removable engagement with the outer surface of the first and second wings.

10. The adjustable brace apparatus of claim 1, wherein each of the first and second tightening segments provides an integral, relatively flat connector portion, a bottom surface of each connector portion configured for removable engagement with the outer surface of the corresponding first or second wing.

11. The adjustable brace apparatus of claim 10, wherein the outer surface of each of the first and second wings provides a plurality of size indicia positioned and configured for assisting the user in consistently positioning each of the first and second tightening segments on the corresponding first and second wings in order to maintain a consistent circumference size.

12. The adjustable brace apparatus of claim 1, wherein an inner surface of the adjustment sleeve provides an at least one elongate, relatively flexible, substantially laterally oriented segment track configured for slidably receiving and retaining an at least one track engagement means provided by the first tightening segment and an at least one further track engagement means provided by the second tightening segment.

13. The adjustable brace apparatus of claim 1, wherein each of the first and second tightening segments provides an at least one longitudinal flexing means configured for allowing the tightening means to selectively flex inwardly, toward the user's body portion, and substantially conform to the contours of the user's body portion during use of the apparatus.

14. The adjustable brace apparatus of claim 1, wherein an inner surface of the adjustment sleeve provides a pocket sized and configured for removably receiving a relatively rigid support insert, the support insert configured for providing further structural and ergonomic support to the user's body portion during use of the apparatus.

15. The adjustable brace apparatus of claim 1, further comprising an at least one relatively rigid wing panel selectively positionable on and removably engagable with one of the first and second wings, the at least one wing panel configured for providing further structural and ergonomic support to the user's body portion during use of the apparatus.

16. An adjustable back brace apparatus comprising:
a pair of elongate first and second wings configured for wrapping about and substantially conforming to a torso of a user.
an adjustment sleeve configured for slidably receiving a first end of each of the first and second wings through opposing ends of the adjustment sleeve;
a tightening means comprising:
  a first tightening segment providing a plurality of spaced apart substantially perpendicular first tightening posts mounted therewithin and an integral, relatively flat first connector portion, a bottom surface of the first connector portion configured for removable engagement with an outer surface of the first wing;
  a second tightening segment providing a plurality of spaced apart substantially perpendicular second tightening posts mounted therewithin and an integral, relatively flat second connector portion, a bottom surface of the second connector portion configured for removable engagement with an outer surface of the second wing;
  a first cord operatively connected to the first tightening segment and a second cord operatively connected to the second tightening segment, each of the first and second cords running around alternating first and second tightening posts in alternation for providing a mechanical force advantage when pulled by the user, dependent upon the number of tightening posts mounted within each tightening segment, to draw the first and second wings closer against the user's torso; and
  each of the first and second tightening segments providing an at least one longitudinal flexing means configured for allowing the tightening means to selectively flex and substantially conform to the contours of the user's torso during use of the apparatus;
  an inner surface of the adjustment sleeve providing an at least one elongate, relatively flexible segment track configured for slidable engagement with a top surface of each of the first and second tightening segments, enabling the first and second tightening segments to substantially float within the adjustment sleeve, thereby further enabling the first and second wings to selectively overlap therewithin;
an opposing free second end of each of the first and second wings providing a means for removable engagement with one another;
whereby, during use of the apparatus, with the adjustment sleeve positioned substantially adjacent a lower back of the user, the first ends of each of the first and second wings slidably inserted into the opposing ends of the adjustment sleeve and overlapped as necessary so as to substantially approximate the circumference of the user's torso, and the tightening means removably engaged with the first and second wings, the user is able to selectively position and wrap the first and second wings around the user's torso, engage the free second ends substantially adjacent an abdomen of the user, and selectively pull the first and second cords to create further compression.

17. An adjustable brace apparatus comprising:
a pair of elongate first and second wings configured for wrapping about and substantially conforming to a portion of a body of a user;
a tightening means comprising:
  a first tightening segment engaged with an outer surface of the first wing and providing a plurality of substantially U-shaped first cord channels, formed by U-shaped walls spaced from a plurality of substantially perpendicular first tightening posts mounted within the first tightening segment;
  a second tightening segment engaged with an outer surface of the second wing and providing a plurality of substantially U-shaped second cord channels, formed by U-shaped walls spaced from a plurality of substantially perpendicular second tightening posts mounted within the second tightening segment;
  each of the first and second tightening posts providing a bearing rotatably engaged therewith;
  an at least one cord operatively running through the first and second cord channels and around the bearings of the first and second tightening posts in alternation, for providing a mechanical force advantage when pulled by the user, dependent upon the number of tightening posts mounted within each tightening segment, to draw the first and second wings closer against the user's body portion; and
  each of the first and second tightening segments providing an at least one longitudinal flexing means configured for allowing the tightening means to selectively flex and substantially conform to the contours of the user's body portion during use of the apparatus; and
an opposing free end of each of the first and second wings providing a means for removable engagement with one another;
whereby, during use of the apparatus, the user is able to selectively position and wrap the first and second wings around the user's body portion, engage the free ends, and selectively pull the at least one cord of the tightening means to create further compression.

18. An adjustable brace apparatus comprising:
an at least one elongate wing configured for wrapping about and substantially conforming to a portion of a body of a user; and
a tightening means comprising:
- a first tightening segment and an opposing second tightening segment each removably engagable with the at least one wing;
- an at least one cord operatively connected to the first and second tightening segments and configured for selectively drawing the at least one wing closer against the user's body portion; and
- a pull ring secured to a free end of the at least one cord and comprising:
  - a thin, relatively resilient first portion defining a first ring aperture sized and configured for allowing the user to insert an at least one finger or thumb therethrough;
  - a thin, relatively rigid second portion integrally secured to a top surface of the first portion and defining a corresponding second ring aperture, the second ring aperture substantially aligned with the first ring aperture and providing a rounded annular inner edge extending a distance through, and substantially obscuring a portion of an inner edge of, the first ring aperture; and
  - the first and second portions together providing a cord capsule therebetween, configured for capturing and protecting the free end of the cord therewithin, the cord extending through a first cord aperture provided by the cord capsule;
whereby, during use of the apparatus, the user is able to selectively position, wrap, and engage the at least one wing around the user's body portion and selectively pull the at least one pull ring of the tightening means to create further compression.

19. The adjustable brace apparatus of claim 18, wherein the first portion provides a second cord aperture positioned and configured for providing access to the free end of the cord within the cord capsule, whereby, the free end of the cord is able to be inserted through both the first and second cord apertures and knotted so that the free end is unable to be pulled back through the first cord aperture, at which point the cord may then be pulled back through the second cord aperture into the cord capsule, where it is substantially preserved from any potential damage or unintentional disengagement.

20. The adjustable brace apparatus of claim 18, wherein the top surface of the first portion of the pull ring provides loop material, an opposing bottom surface of the first portion provides hook material, and the second ring aperture of the second portion is sized and configured for allowing at least partial access to the loop material on the top surface of the first portion.

* * * * *